United States Patent
Mitch et al.

(10) Patent No.: US 6,284,771 B1
(45) Date of Patent: Sep. 4, 2001

(54) METHOD FOR TREATING SCHIZOPHRENIA

(75) Inventors: Charles H. Mitch, Columbus, IN (US); Per Sauerberg, Farum (DK); Harlan E. Shannon, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/403,061
(22) PCT Filed: Apr. 10, 1998
(86) PCT No.: PCT/US98/07199
   § 371 Date: Apr. 3, 2000
   § 102(e) Date: Apr. 3, 2000
(87) PCT Pub. No.: WO98/46226
   PCT Pub. Date: Oct. 22, 1998

Related U.S. Application Data
(60) Provisional application No. 60/043,567, filed on Apr. 11, 1997.

(51) Int. Cl.$^7$ ..................................................... A61K 31/44
(52) U.S. Cl. ...................... 514/305; 514/299; 514/214.03
(58) Field of Search ..................................... 514/305, 299, 514/214.03

(56) References Cited

U.S. PATENT DOCUMENTS

| 5,418,240 | * | 5/1995 | Sauerburg et al. | 514/305 |
| 5,545,740 | * | 8/1996 | Hughes et al. | 546/112 |
| 5,677,313 | * | 10/1997 | Bymaster et al. | 514/304 |

FOREIGN PATENT DOCUMENTS

0392803  * 10/1990  (EP) ..................................... 514/305

* cited by examiner

*Primary Examiner*—James H. Reamer
(74) *Attorney, Agent, or Firm*—David M. Stemerick; Arleen Palmberg

(57) ABSTRACT

The present invention provides a method for treating a condition selected from the group consisting of schizophrenia, schizoaffective disorder, and schizophreniform disorder in a patient using a Compound (I).

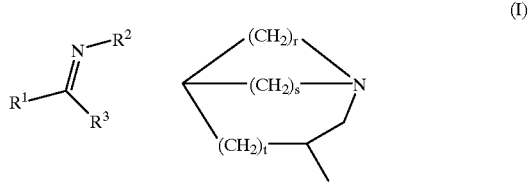

9 Claims, No Drawings

METHOD FOR TREATING SCHIZOPHRENIA

This application is a 371 of PCT/US98/07199 filed Apr. 10, 1998 which claim benefit of Ser. No. 60/043,567 filed Apr. 11, 1997.

FIELD OF THE INVENTION

This invention provides a method for treating or alleviating the symptoms of pathologic psychosis, comprising administering an effective amount of a cyano-oxime compound.

BACKGROUND OF THE INVENTION

The method of this invention provides a method for treating schizophrenia using compounds which were previously disclosed for use in the treatment of Alzheimer's Disease. The method of this invention provide the clinician with another treatment option for the treatment of psychotic conditions. The compounds used in the presently claimed method appear to have an acceptable side effect profile while providing surprising anti-psychotic activity.

SUMMARY OF THE INVENTION

The present invention provides a method for treating a condition selected from the group consisting of schizophrenia, schizophreniform disorder, and schizoaffective disorder, comprising administering an effective amount of Compound I:

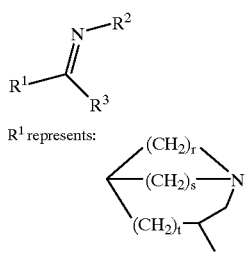

wherein
r represents an integer of 2 to 4, s represents 1 or 2 and t represents 0 or 1;
$R^2$ is a group $OR^4$, where $R^4$ is $C_{1-4}$ alkyl, $C_{2-4}$ alkenyl, $C_{2-4}$ alkynyl, a group $OCOR^5$ where $R^5$ is hydrogen or $R^4$; and $R^3$ is CN; or
a pharmaceutically acceptable salt or solvate thereof.

The present invention provides a method for treating a condition selected from the group consisting of Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive SubstanHallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Personality Disorder (310.10), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39); Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Personality Disorders, Paranoid (301.00), Personality Disorders, Schizoid (301.20), Personality Disorders, Schizotypal (301.22), Personality Disorders, Antisocial (301.70), and Personality Disorders, Borderline (301.83) comprising administering an effective amount of Compound I or a pharmaceutically acceptable salt thereof.

DETAILED DESCRIPTION

As noted hereinbefore, the cyano-oxime compounds referred to herein as Compound I, employed in the method of the present invention are known. The compounds, methods of preparing the compounds, as well as pharmaceutical formulations containing the compounds, are taught by published Paris Convention Treaty Application (PCT) number WO95/31456. Thus, the artisan can readily prepare the Compound I materials described herein using the teachings in the published patent applications. To further clarify, Compound I shall refer to a compound of the structure:

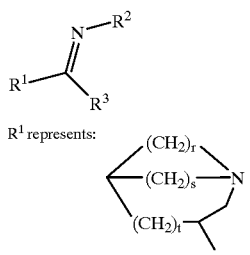

(I)

wherein r represents an integer of 2 to 4, s represents 1 or 2 and t represents 0 or 1;

$R^2$ is a group $OR^4$, where $R^4$ is $C_{1-4}$ alkyl, $C_{2-4}$ alkenyl, $C_{2-4}$ alkynyl, a group $OCOR^5$ where $R^5$ is hydrogen or $R^4$; and $R^3$ is CN; or a pharmaceutically acceptable salt or solvate thereof. A particularly preferred Compound I is of the formula II:

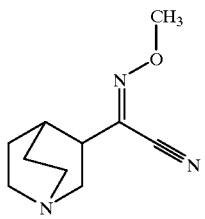

II

An especially preferred compound is known as SB202026.

The term "alkyl" refers to the number of carbon atoms indicated; however, when no number is specified, the term refers to $C_{1-6}$ alkyl. The alkyl may be linear or branched unless specified.

The term "alkynyl" has its accepted meaning; however, if the number of carbon atoms are unspecified, it refers to $C_{2-10}$ alkynyl. The alkynyl group may be linear or branched unless specified.

The term "psychotic condition" refers to a condition wherein hallucinations, delusions, and/or confused thought process are characteristic manifestations of the named condition.

The term "pathologic" refers to a clinically significant disease state.

The term "effective amount", as used herein, represents an amount of compound necessary to prevent or treat a human susceptible to or suffering from a psychotic condition following administration to such human. The active compound is effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

The compound may further be delivered by a variety of other pharmaceutically accepted routes including, but in no way limited to parenterally, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed physical and/or mental condition once it has been established or alleviation of the characteristic symptoms of such condition.

Pathologic psychological conditions which are psychoses or may be associated with psychotic features include, but are not limited to the following disorders which have been characterized in the DSM-III-R. *Diagnostic and Statistical Manual of Mental Disorders, Revised,* 3rd Ed. (1980). The DSM-III-R was prepared by the Task Force on Nomenclature and Statistics of the American Psychiatric Association, and provides clear descriptions of diagnostic catagories. The numbers in parenthesis refer to the DSM-III-R categories. The skilled artisan will recognize that there are alternative nomenclatures, nosologies, and classification systems for pathologic psychological conditions and that these systems evolve with medical scientific progress.

Examples of pathologic psychologic conditions which may be treated using Compound I include, but are not limited to, Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive SubstanHallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Personality Disorder (310.10), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39); Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Personality Disorders, Paranoid (301.00), Personality Disorders, Schizoid (301.20), Personality Disorders, Schizotypal (301.22), Personality Disorders, Antisocial (301.70), and Personality Disorders, Borderline (301.83)

As mentioned above, Compound I has useful antipsychotic activity. This activity can be demonstrated in models using well-established procedures. For example, the compound is assessed in a number of standard behavioral tests predictive of antipsychotic activity. Antagonism of apomorphine-induced climbing behavioral and hypothermia in mice is predictive of antipsychotic activity (see, Moore, N.A. et al. Psychopharmacology 94 (2), 263–266 (1988), and 96, 539 (1988)). Further, the conditioned avoidance model, as described by Davidson, A. B. *Differential Effect of Neuroleptic and other Psychotropic Agents on Acquisition of Avoidance in Rats,* 18 *Life Sci.* 127901284 (1976).

One of the major pharmacological properties of currently employed clinical antipsychotic drugs in animals is their ability to block conditioned avoidance responding (Cook and Davidson, Psychopharmacology, A Generation of Progress, (Raven Press, New York: 1978) pp 563–567; Davidson and Weidley, *Life Sci.* 18:1279–1284, 1976).

There is a high correlation between their activity and potency on a conditioned avoidance test and their clinical efficacy and potencies as antipsychotic drugs (Creese et al, *Dopamine receptor binding predicts clinical and pharmacological properties of antischizophrenic drugs Science* 192:481–483, 1976).

In the conditioned avoidance test, animals learn to respond during a conditioned stimulus in order to avoid mild shock presentation. A response during the conditioned stimulus is termed an avoidance response, a response during shock is termed an escape response; a response failure is when the animal fails to respond either during the conditioned stimulus or the shock presentation and is indicative of motor impairment. Animals rapidly learn to avoid 99% of the time. Antipsychotic drugs decrease the percentage of avoidance without interfering with the ability of the animal to respond since the animals do emit escape responses. The percentage of response failures is considered a measure of motor impairment.

Procedure

Rats were required to press a response lever in an experimental chamber in order to avoid or escape foot-shock. Each experimental session consisted of 50 trials. During each trial, the chamber was illuminated and a tone presented for a maximum of 10 seconds. A response during the tone immediately terminated the tone and the houselight, ending the trial. In the absence of a response during the tone alone, tone plus foot shock (2.0 mA) was presented for a maximum of 10 seconds. A response during shock presentation immediately terminated the shock, the tone and the houselight, ending the trial.

Such studies suggest that Compound I may be especially desirable for the treatment of schizophrenia.

For drug screening, a dose of 3.0 mg/kg was administered s.c. 30 minutes before the start of the experimental session. A drug was considered active if it reduced the percent avoidance responding to at least 50% without producing greater than 50% response failures. For active drugs, a dose response curve was subsequently determined.

The following Examples are studies to establish the usefulness of the named compounds for treating such psychotic conditions.

EXAMPLE 1

Human Clinical Trials

The activity of Compound I for treating or alleviating psychosis can be demonstrated by human clinical trials. The study was designed as a double-blind, parallel, placebo-controlled multicenter trial. The patients are randomized into four groups, placebo and 3 other dosages of test compound. The dosages are administered orally with food. Patients are observed at four visits to provide baseline measurements. Visits 5–33 served as the treatment phase for the study.

During the visits, patients are observed for signs of agitation, mood swings, tremor, delirium, social withdrawal, and concentration abilities. These behaviors are indicative of the effect of the test compound on psychotic conditions.

Treatment groups are compared with respect to the number and percent of patients who ever had the symptom during the double-blind portion of the study (visits 5 through 33), at a severity that was worse than during the baseline visits (1 through 4).

We claim:

1. A method for treating in a patient suffering from a condition selected from the group consisting of schizophrenia, schizophreniform disorder, and schizoaffective disorder comprising administering to a patient in need thereof, an effective amount of a Compound I:

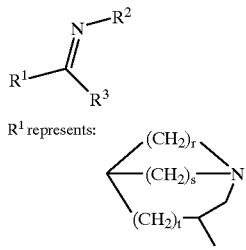

(I)

wherein
  r represents an integer of 2 to 4, s represents 1 or 2 and t represents 0 or 1;
  $R^2$ is a group $OR^4$, where $R^4$ is $C_{1-4}$ alkyl, $C_{2-4}$ alkenyl, $C_{2-4}$ alkynyl, a group $OCOR^5$ where $R^5$ is hydrogen or $R^4$; and $R^3$ is CN; or
a pharmaceutically acceptable salt or solvate thereof
or a pharmaceutically acceptable salt thereof.

2. A method of claim 1 wherein the Compound I is

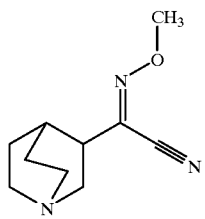

II

3. A method of claim 2 wherein the effective amount is from 1 mg/kg to about 100 mg/kg per day.

4. A method of claim 1 wherein the effective amount is delivered using a transdermal patch.

5. A method of claim 4 wherein the transdermal patch delivers from about 10 to about 100 mg of base compound per day.

6. A method of claim 5 wherein the transdermal patch delivers an effective amount for one (1) to seven (7) days.

7. A method for treating in a patient suffering from a pathologic psychotic condition comprising administering to a patient in need thereof, an effective amount of a Compound I:

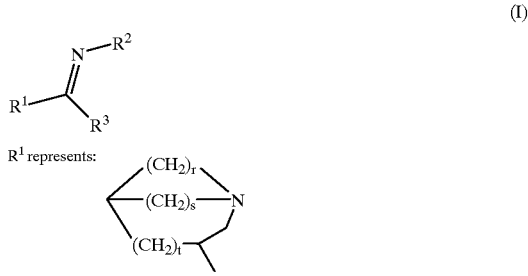

(I)

wherein
  r represents an integer of 2 to 4, s represents 1 or 2 and t represents 0 or 1;
  $R^2$ is a group $OR^4$, where $R^4$ is $C_{1-4}$ alkyl, $C_{2-4}$ alkenyl, $C_{2-4}$ alkynyl, a group $OCOR^5$ where $R^5$ is hydrogen or $R^4$; and $R^3$ is CN; or
a pharmaceutically acceptable salt or solvate thereof
or a pharmaceutically acceptable salt thereof.

8. A method of claim 7 wherein Compound I is

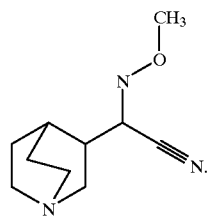

9. A method of claim 8 wherein the pathologic psychotic condition is selected from the group consisting of Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive SubstanHallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Personality Disorder (310.10), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39); Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Personality Disorders, Paranoid (301.00), Personality Disorders, Schizoid (301.20), Personality Disorders, Schizotypal (301.22), Personality Disorders, Antisocial (301.70), and Personality Disorders, Borderline (301.83).

\* \* \* \* \*